United States Patent [19]

Yazawa et al.

[11] Patent Number: 5,608,080
[45] Date of Patent: *Mar. 4, 1997

[54] PROCESS FOR PRODUCTION OF 2-SUBSTITUTED BENZO[B]THIOPHENE

[75] Inventors: Naoto Yazawa; Yoshinori Saito; Hidetaka Hiyoshi, all of Shizuoka-ken, Japan

[73] Assignee: Ihara Chemical Industry Co., Ltd., Tokyo, Japan

[ * ] Notice: The term of this patent shall not extend beyond the expiration date of Pat. No. 5,266,705.

[21] Appl. No.: 424,504

[22] PCT Filed: Sep. 26, 1994

[86] PCT No.: PCT/JP94/01578

§ 371 Date: May 22, 1995

§ 102(e) Date: May 22, 1995

[87] PCT Pub. No.: WO95/09165

PCT Pub. Date: Apr. 6, 1995

[30] Foreign Application Priority Data

Sep. 27, 1993 [JP] Japan .................... 5-264150

[51] Int. Cl.⁶ .................................. C07D 233/56
[52] U.S. Cl. .................................. 549/57
[58] Field of Search .................................. 549/57

[56] References Cited

U.S. PATENT DOCUMENTS

| | | | |
|---|---|---|---|
| 2,761,873 | 9/1956 | Gregory et al. | 549/57 |
| 4,143,052 | 3/1979 | Barrault et al. | 549/49 |
| 5,169,961 | 12/1992 | Dickman et al. | 549/57 |
| 5,266,705 | 11/1993 | Yazawa et al. | 549/57 |
| 5,292,894 | 3/1994 | Ebel et al. | 549/49 |
| 5,298,630 | 3/1994 | Kagano et al. | 549/57 |
| 5,376,677 | 12/1994 | Trah | 549/57 |
| 5,403,939 | 4/1995 | Yazawa et al. | 549/57 |

*Primary Examiner*—Richard L. Raymond
*Assistant Examiner*—Deborah Lambkin
*Attorney, Agent, or Firm*—Oblon, Spivak, McClelland, Maier & Neustadt, P.C.

[57] ABSTRACT

The present invention provides a process for producing a 2-substituted benzo[b]thiophene, which is characterized by reacting a substituted or unsubstituted 2-halogenobenzaldehyde with sulfur and a compound represented by general formula (1)

$$H_iS_jM_k \tag{1}$$

(wherein M represents an alkali metal; i represents an integer of 0 or 1; j represents an integer of 1 or more; and k represents an integer of 1–2 with a proviso that i+k=2), or with a compound of general formula (1) wherein j is 2 or more, in the presence of an aprotic polar solvent, and then reacting the reaction mixture with a compound represented by general formula (2)

$$XCH_2R \tag{2}$$

(wherein X represents a halogen atom; and R represents an acyl group, a substituted or unsubstituted alkoxycarbonyl group, a substituted or unsubstituted arylcarbonyl group or a cyano group) to give rise to intramolecular ring closure.

The present process uses no unstable raw materials; enables production of an intended product in a simple operation at a high yield; and is very effective as a process for industrial production of 2-substituted benzo[b]thiophene.

1 Claim, No Drawings

PROCESS FOR PRODUCTION OF 2-SUBSTITUTED BENZO[B]THIOPHENE

This application is a 371 PCT/JP94/01578 Aug. 26, 1994.

1. Technical Field

The present invention relates to a process for industrially producing a 2-substituted benzo[b]thiophene which is useful, for example, as an intermediate for drug synthesis.

2. Background Art

For the production of 2-substituted benzo[b]thiophene, there is proposed a process which comprises reacting benzo[b]thiophene with a strong base such as butyl lithium or the like and reacting the reaction mixture with an acid chloride such as acetyl chloride or the like to obtain a 2-acylbenzo[b]thiophene [J. Chem. Soc., Chem. Comun., 3447 (1971)].

The above process, however, has problems in that the use of butyl lithium (which is difficult to handle) in the reaction makes the industrial operation difficult and moreover benzo[b]thiophene and butyl lithium both used as raw materials are expensive.

A process is also known which comprises reacting 2-mercaptobenzaldehyde with an α-haloketone such a s chloroacetone or the like to obtain a 2-acylbenzo[b]thiophene (Comptes rendus, Vol. 234,736).

This process, however, has problems in that the industrial synthesis of 2-mercaptobenzaldehyde used as a raw material is difficult and moreover this compound is unstable and needs careful handling.

The task of the present invention is to provide a process for industrially producing a 2-substituted benzo[b]thiophene inexpensively.

DISCLOSURE OF THE INVENTION

The present inventors made a study on the process for industrial production of 2-substituted benzo[b]thiophene. As a result, the present inventors unexpectedly found out that the conventional problems could be solved and a 2-substituted benzo[b]thiophene could easily be produced by reacting a 2-halogenobenzaldehyde of high commercial availability with a particular inorganic sulfur compound and reacting the reaction mixture with a compound represented by general formula (2) (shown below) to give rise to intramolecular ring closure. The present invention has been completed based on the above finding.

The present invention provides a process for producing a 2-substituted benzo[b]thiophene, which is characterized by reacting a substituted or unsubstituted 2-halogenobenzaldehyde with sulfur and a compound represented by general formula (1)

$$H_iS_jM_k \quad (1)$$

(wherein M represents an alkali metal; i represents an integer of 0 or 1; j represents an integer of 1 or more; and k represents an integer of 1–2 with a proviso that i+k=2), or with a compound of general formula (1) wherein j is 2 or more, in the presence of an aprotic polar solvent, and then reacting the reaction mixture with a compound represented by general formula (2)

$$XCH_2R \quad (2)$$

(wherein X represents a halogen atom; and R represents an acyl group, a substituted or unsubstituted alkoxycarbonyl group, a substituted or unsubstituted arylcarbonyl group or a cyano group) to give rise to intramolecular ring closure.

BEST MODE FOR CARRYING OUT THE INVENTION

The present invention is described in detail below.

The present invention comprises a first reaction of reacting a substituted or unsubstituted 2-halogenobenzaldehyde (which may hereinafter be referred to simply as 2-halogenobenzaldehydes) with sulfur and a compound represented by general formula (1), or with a compound of general formula (1) wherein j is 2 or more, in the presence of an aprotic polar solvent to obtain a reaction mixture, and a second reaction of reacting the reaction mixture obtained in the first reaction, with a compound represented by general formula (2) to give rise to intramolecular ring closure to obtain a 2-substituted benzo [b]thiophene.

Description is made firstly on the aprotic polar solvent used throughout the first and second reactions of the present invention.

Specific examples of the aprotic polar solvent used throughout the first and second reactions of the present invention are N-methylpyrrolidone, N-octylpyrrolidone, 1,3-dimethylimidazolidinone, diethylacetamide, dimethylacetamide, dimethylformamide, dimethyl sulfoxide, sulfolane, tetramethylurea, hexamethylphosphoric triamide and N-methyl-N-phenylformamide. These aprotic polar solvents can be used in any combination of two or more of them.

In the present process there may be used, as the reaction solvent, a mixed solvent consisting of the aprotic polar solvent and another solvent which is inactive in the reactions. Specific examples of another solvent are aromatic hydrocarbon solvents such a s benzene, toluene, xylene, chlorobenzene and dichlorobenzene.

In the present process, the amount of the solvent used is sufficient if it can ensure stirring. The amount is ordinarily 100–3,000 ml per mole of the 2-halogenobenzaldehydes.

Next, description is made on the first reaction of the present process.

The 2-halogenobenzaldehydes usable in the first reaction include benzaldehydes whose 2-position is substituted with a halogen atom such as fluorine atom, chlorine atom, bromine atom, iodine atom or the like (hereinafter, halogen atom has the same definition) and at least one position of the 3-to 6-positions of these benzaldehydes may be substituted with unrestricted group(s) such as halogen atom(s), nitro group(s), cyano group(s) and the like.

Of the compounds of general formula (1) used in the first reaction, the compound wherein j is 1, i.e. the monosulfur compound can specifically be exemplified by potassium sulfide, sodium sulfide, potassium hydrosulfide and sodium hydrosulfide; and the compound wherein j is 2 or more, i.e. the polysulfur compound can specifically be exemplified by sodium polysulfides and potassium polysulfides, more specifically by sodium disulfide, sodium trisulfide, sodium tetrasulfide, sodium pentasulfide, potassium disulfide, potassium trisulfide, potassium tetrasulfide and potassium pentasulfide. A combination example of sulfur and the compound represented by general formula (1) is a combination of sulfur and a monosulfur compound or a polysulfur compound.

It is possible to use, as necessary, two or more of the compounds represented by general formula (1).

In the first reaction, when the compound of general formula (1) is used in combination with sulfur, the amount of said compound used is ordinarily 0.5–10 moles, preferably 1–3.5 moles per mole of the 2-halogenobenzaldehydes, and the amount of sulfur used is ordinarily 10 moles or less, preferably 3.5 moles or less per mole of the 2-halogenobenzaldehydes. When no sulfur is used and there is used only the compound of general formula (1) wherein j is 2 or more, the amount of said compound used is ordinarily 0.5–10 moles, preferably 1–3.5 moles per mole of the 2-halogenobenzaldehydes.

When the compound of general formula (1) is used in combination with sulfur, it is preferable that the compound of general formula (1) and sulfur are stirred beforehand in an aprotic polar solvent in the range from room temperature to 50° C. for 0.5–3 hours.

In the first reaction, it is possible to employ any order of adding the 2-halogenobenzaldehydes, and the compound of general formula (1) and sulfur or only the compound of general formula (1) wherein j is 2 or more. However, the pattern of adding the 2-halogenobenzaldehydes gives a more favorable result.

In the first reaction, the reaction temperature is any temperature in the range from 0° C. to the boiling point of the solvent, preferably in the range of 0°–80° C. While the completion of the reaction can be confirmed by examining the disappearance of the 2-halogenobenzaldehydes by gas chromatography, the reaction time is generally 3–24 hours.

Subsequently, description is made on the second reaction of the present process.

The compound represented by general formula (2), used in the second reaction can be exemplified by α-halocarbonyl compounds and halogenonitrile compounds. The α-halocarbonyl compounds are specifically monohalogenoacetone compounds such as chloroacetone, bromoacetone and the like; halogenoalkanoic acid ester compounds such as methyl, ethyl, propyl, isopropyl, butyl, isobutyl, sec-butyl, tert-butyl, pentyl, isopentyl, neopentyl, amyl, isoamyl, tert-amyl, sec-isoamyl, hexyl or isohexyl esters of monochloroacetic acid, monobromoacetic acid, monoiodoacetic acid, monochloropropionic acid, monobromopropionic acid, monoiodopropionic acid, monochlorobutanoic acid, monobromobutanoic acid, monoiodobutanoic acid, monochloropentanoic acid, monobromopentanoic acid, monoiodopentanoic acid, monochlorohexanoic acid, monobromohexanoic acid and monoiodohexanoic acid; and phenacyl halide compounds (arylcarbonylmethyl halide compounds) such as 2-chloroacetophenone, 2-chloroacetonaphthone, 2-chloro-2'-methylacetophenone, 2-bromoacetophenone, 2-bromoacetonaphthone, 2-bromo-2'-methylacetophenone, 2iodoacetophenone, 2-iodoacetonaphthone, 2-iodo-2'-methylacetophenone and the like. The halogenonitrile compounds are specifically chloroacetonitrile, bromoacetonitrile, iodoacetonitrile, chloropropionitrile, bromopropionitrile, chlorobutyronitrile, bromobutyronitrile and the like.

In the second reaction, the amount of the compound of general formula (2) used is generally 0.5–10 moles, preferably 1–2 moles per mole of the 2-halogenobenzaldehydes.

The second reaction proceeds in any order of adding the compound of general formula (2) and the reaction mixture formed in the first reaction. However, in view of the easiness of the operation, etc., generally the compound of general formula (2) is added into the vessel of the first reaction containing the reaction mixture obtained in the first reaction, and the first reaction and the second reaction are conducted continuously in the same vessel.

In the second reaction, the temperature at which the compound of general formula (2) is allowed to act on the reaction mixture formed in the first reaction is not specified. However, since the reaction is an exothermic reaction, the temperature is preferably kept in the range of 0°–80° C. by cooling as necessary. The time in which the compound is allowed to act, is generally 1–16 hours to achieve the object although the time varies depending upon various factors such as raw materials, solvent, reaction temperature, etc. used.

The rate of the intramolecular ring closure reaction taking place subsequently to the substitution reaction is small in some cases depending upon the kind of the compound of general formula (2) used in the second reaction. In such cases, addition of a strong base such as metal alcoholate (e.g. sodium methylate, sodium ethylate or potassium methylate) can increase said rate to quickly obtain an intended ring closure product, i.e. a 2-substituted benzo[b]thiophene.

As a result, the time required in the present process throughout the first reaction and the second reaction is generally 4–43 hours although it varies depending upon the compounds, reaction conditions, etc. used.

In the present process, the intended product obtained may be recrystallized from an appropriate solvent such as cyclohexane, alcohol-water mixture or the like or subjected to distillation to obtain a 2-substituted benzo[b]thiophene of higher purity.

When the 2-position substituent of the obtained 2-substituted benzo[b]thiophene is an alkoxycarbonyl group or a cyano group, the compound is hydrolyzed by an ordinary method, whereby benzo[b]thiophene-2-carboxylic acid can easily be obtained. This benzo[b]thiophene-2-carboxylic acid can easily be converted into benzo[b]thiophene having no substituent at the 2-position by subjecting to a decarboxylation treatment in a quinoline solvent in the presence of a copper catalyst at about 200°–300° C. When the 2-position substituent is a cyano group, the 2-substituted benzo[b]thiophene is hydrolyzed under appropriately altered conditions, whereby benzo[b]thiophene-2-carboxamide can be produced.

EXAMPLES

The present invention is described more specifically below by way of Examples.

EXAMPLES 1–2

Into a 200-ml four-necked flask equipped with a stirrer, a thermometer and a reflux condenser were fed 11.7 g (150 mM) of anhydrous sodium sulfide, 3.2 g (100 mM) of sulfur and 100 ml of N-methylpyrrolidone. The mixture was stirred at room temperature for 1 hour. To the mixture was dropwise added 100 mM of a 2-halogenobenzaldehyde shown in Table 1. The mixture was stirred at room temperature for 12 hours. To the reaction mixture being water-cooled was dropwise added 120 mM of a compound of general formula (2) shown in Table 1. The mixture was stirred at room temperature for 6 hours to give rise to a reaction. After the completion of the reaction, 100 ml of diethyl ether and 100 ml of water were added to the reaction mixture. Further, an aqueous sodium hydroxide solution was added to allow the aqueous layer to have a pH of above 11. Then, extraction with diethyl ether was conducted. The resulting diethyl ether layer was water-washed twice and concentrated under reduced pressure to remove diethyl ether to obtain a 2-substituted benzo[b]thiophene. The 2-halogenobenzaldehydes and compound of general formula (2) used in Each Example, the product and the yield are shown in Table 1.

TABLE 1

| Example No. | 2-Halogeno-benzaldehydes | Compound of general formula (2) | Product | Yield* (%) |
|---|---|---|---|---|
| 1 |  | ClCH₂COPh | | 71 |
| 2 |  | ClCH₂COCH₃ | | 95 |

*Obtained by gas chromatography.

In the above table, Ph refers to phenyl group.

Example 3

Into a 200-ml four-necked flask equipped with a stirrer, a thermometer and a reflux condenser were fed 14.1 g (0.18 mole) of anhydrous sodium sulfide, 5.8 g (0.18 mole) of sulfur and 45 ml of dimethylformamide. The mixture was stirred at room temperature. Heat generation occurred and the mixture temperature increased to 45° C. After the completion of the heat generation, 21.1 g (0.15 mole) of 2-chlorobenzaldehyde was dropwise added in 10 minutes at 70°–75° C. with slight heating. The mixture was stirred at the same temperature for 4 hours. The reaction mixture was cooled to room temperature. To the mixture being stirred was dropwise added 16.3 g (0.15 mole) of methyl chloroacetate in 10 minutes under spontaneous heat generation. The mixture was stirred at 55°–60° C. for 1.5 hours. 8.1 g (0.15 mole) of sodium methoxide was added at the same temperature, followed by stirring for 30 minutes. The reaction mixture was analyzed by gas chromatography, which indicated the formation of methyl benzo[b]thiophene-2-carboxylate in an amount of 86% by areal ratio. The reaction mixture was stirred for a further 1 hour. 40 ml of water and 6 g of 48% sodium hydroxide were added and the mixture was stirred at 95° C. for 1.5 hours to give rise to hydrolysis. After the completion of the reaction, dilution with 100 ml of water was conducted. 100 ml of toluene was added and extraction was conducted at 75° C. to remove neutral components. The aqueous layer was placed in a 1-litter beaker. Thereto was dropwise added 22.1 g (0.21 mole) of 95% sulfuric acid with stirring. The resulting crystals were collected by filtration and dried to obtain 17.6 g of crude benzo[b]thiophene-2-carboxylic acid. This product was washed with toluene and redried to obtain 17.1 g of benzo[b]thiophene-2-carboxylic acid. The yield was 64.0% and the purity was 99.7%.

Example 4

A reaction up to the formation of a ring closure product was conducted in the same manner as in Example 3 except that 11.3 g (0.15 mole) of chloroactonitrile was used in place of methyl chloroacetate, the amount of sodium methoxide used was changed to 4.1 g and, after the addition of sodium methoxide, stirring was conducted at 70° C. for 3 hours to complete the reaction. The reaction mixture was placed in 400 ml of water, and extraction with 300 ml of toluene was conducted. The toluene layer was washed twice with 400 ml of water. The organic layer was dried with anhydrous sodium sulfate and concentrated to obtain 13.2 g of 2-cyanobenzo[b]thiophene. Yield: 55.3% )

Industrial Applicability

The present invention provides a novel process for producing a 2-substituted benzo[b]thiophene, which is characterized by reacting 2-halogenobenzaldehydes of high commercial availability with a compound represented by general formula (1) and sulfur or with a compound represented by general formula (1) wherein j is 2 or more, and then reacting the reaction mixture with a compound represented by general formula (2) to give rise to intramolecular ring closure.

Therefore, the present process involves no handling of any raw material and intermediate which are unstable and difficult to handle industrially; can produce a 2-substituted benzo[b]thiophene from raw materials of high availability and low cost, in a simple operation at a high yield; and is very effective as a process for industrial production of 2-substituted benzo[b]thiophene.

We claim:

1. A process for producing a 2-substituted benzothiophene, which is characterized by reacting a substituted or unsubstituted 2-halogenobenzaldehyde with sulfur and a compound represented by general formula (1)

$$H_iS_jM_k \qquad (1)$$

(wherein M represents an alkali metal; i represents an integer of 0 or 1; j represents an integer of 1 or more; and k represents an integer of 1–2 with a proviso that i+k=2), or with a compound of general formula (1) wherein j is 2 or more, in the presence of an aprotic polar solvent, and then reacting the reaction mixture with a compound represented by general formula (2)

$$XCH_2R \qquad (2)$$

(wherein X represents a halogen atom; and R represents an acyl group, a substituted or unsubstituted alkoxycarbonyl group, a substituted or unsubstituted arylcarbonyl group or a cyano group) to give rise to intramolecular ring closure.

* * * * *